United States Patent
Singh

(10) Patent No.: US 7,987,700 B2
(45) Date of Patent: Aug. 2, 2011

(54) APPARATUS FOR MEASURING OSMOTIC PRESSURE, CONDUCTANCE, VISCOSITY AND SURFACE TENSION OF LIQUID SOLUTION

(76) Inventor: Man Singh, New Delhi (IN)

(*) Notice: Subject to any disclaimer, the term of this patent is extended or adjusted under 35 U.S.C. 154(b) by 512 days.

(21) Appl. No.: 12/226,343

(22) PCT Filed: Apr. 17, 2007

(86) PCT No.: PCT/IB2007/000991
§ 371 (c)(1),
(2), (4) Date: Oct. 17, 2008

(87) PCT Pub. No.: WO2007/119161
PCT Pub. Date: Oct. 25, 2007

(65) Prior Publication Data
US 2009/0229350 A1 Sep. 17, 2009

(30) Foreign Application Priority Data
Apr. 17, 2006 (IN) .............................. 999/DEL/2006

(51) Int. Cl.
*G01N 11/00* (2006.01)
*G01N 13/00* (2006.01)
*G01N 13/04* (2006.01)
(52) U.S. Cl. ..................... 73/53.01; 73/54.02; 73/64.52; 73/64.47
(58) Field of Classification Search ............... 73/64.47, 73/54.02, 64.52
See application file for complete search history.

(56) References Cited

U.S. PATENT DOCUMENTS

| 4,361,032 A | 11/1982 | Lessnig et al. |
| 5,005,403 A * | 4/1991 | Steudle et al. ............ 73/61.71 |
| 6,085,577 A | 7/2000 | Christensen et al. |
| 6,298,713 B1 * | 10/2001 | Nandu et al. ............ 73/64.47 |

FOREIGN PATENT DOCUMENTS

| DE | 30 14 705 A1 | 10/1981 |
| DE | 199 63 686 A1 | 7/2001 |
| FR | 665 409 | 9/1929 |
| FR | 2 373 050 | 6/1978 |
| JP | 02226045 A * | 9/1990 |

* cited by examiner

*Primary Examiner* — Hezron Williams
*Assistant Examiner* — Nathaniel Kolb
(74) *Attorney, Agent, or Firm* — Oliff & Berridge, PLC

(57) ABSTRACT

The present invention provides an apparatus (Oscosurvismeter) for measuring osmotic pressure, surface tension, viscosity and conductance. Oscosurvismeter is made of Borosil glass material for measuring osmotic pressure, specific conductance, viscosity and surface tension of solutions. Solutions of different strengths are taken in two cells/compartments, partitioned by semi permeable membrane (SPM), respectively. Concentration gradient makes the solvent move towards concentrated solution to establish equilibrium that measures osmotic pressure. The Oscosurvismeter saves time and material, and enhances accuracy and precision in measurements, the instrument consists of six parts: Survismeter, Osmometer, Electrode, Metallic clamp, Semipermeable membrane (SPM), and High Potential metallic springs. The high accuracies data are noted with the instrument.

8 Claims, 2 Drawing Sheets

ASSEMBLY DRAWING OF OSCOSURVISMETER

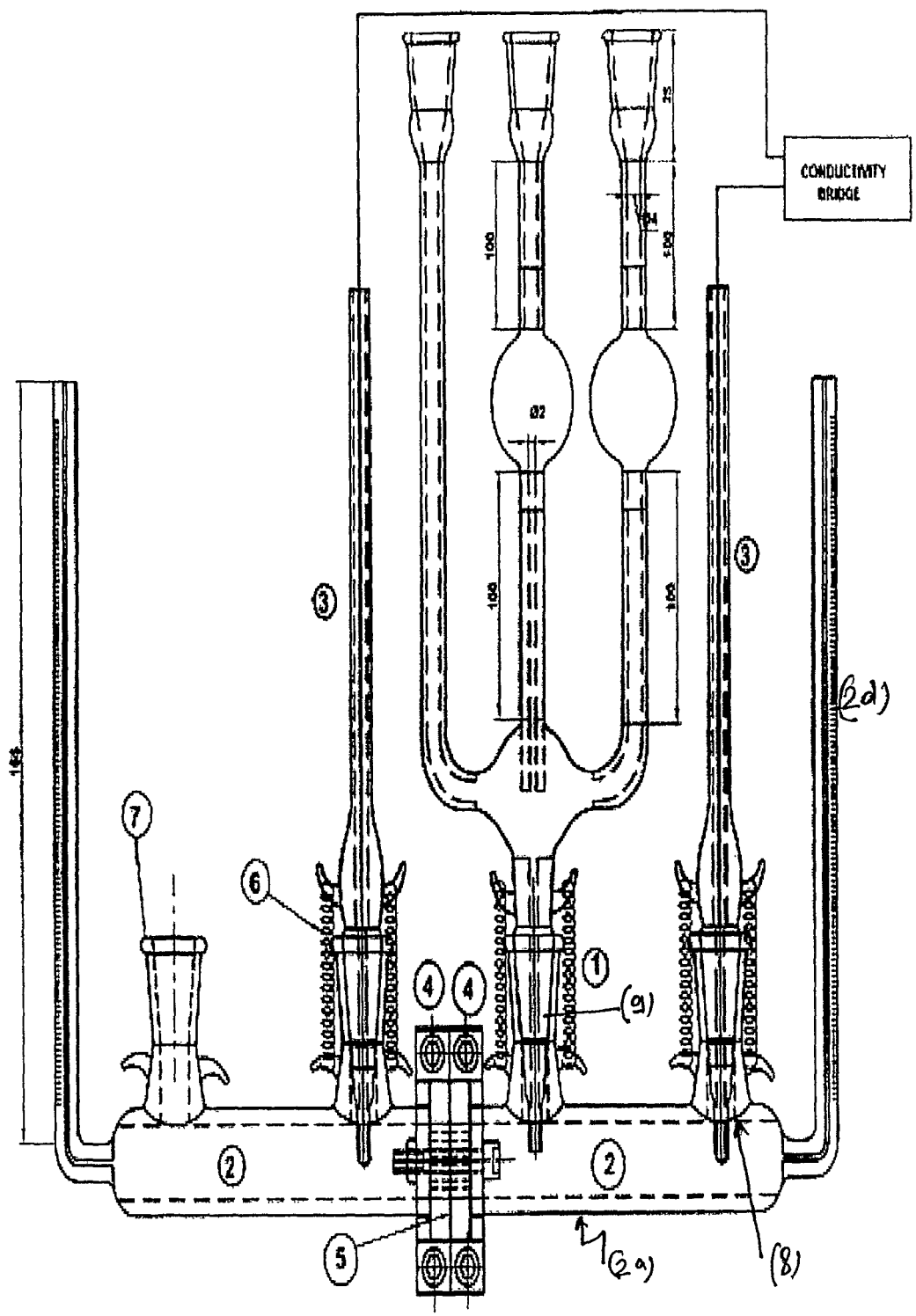
Figure 1: ASSEMBLY DRAWING OF OSCOSURVISMETER

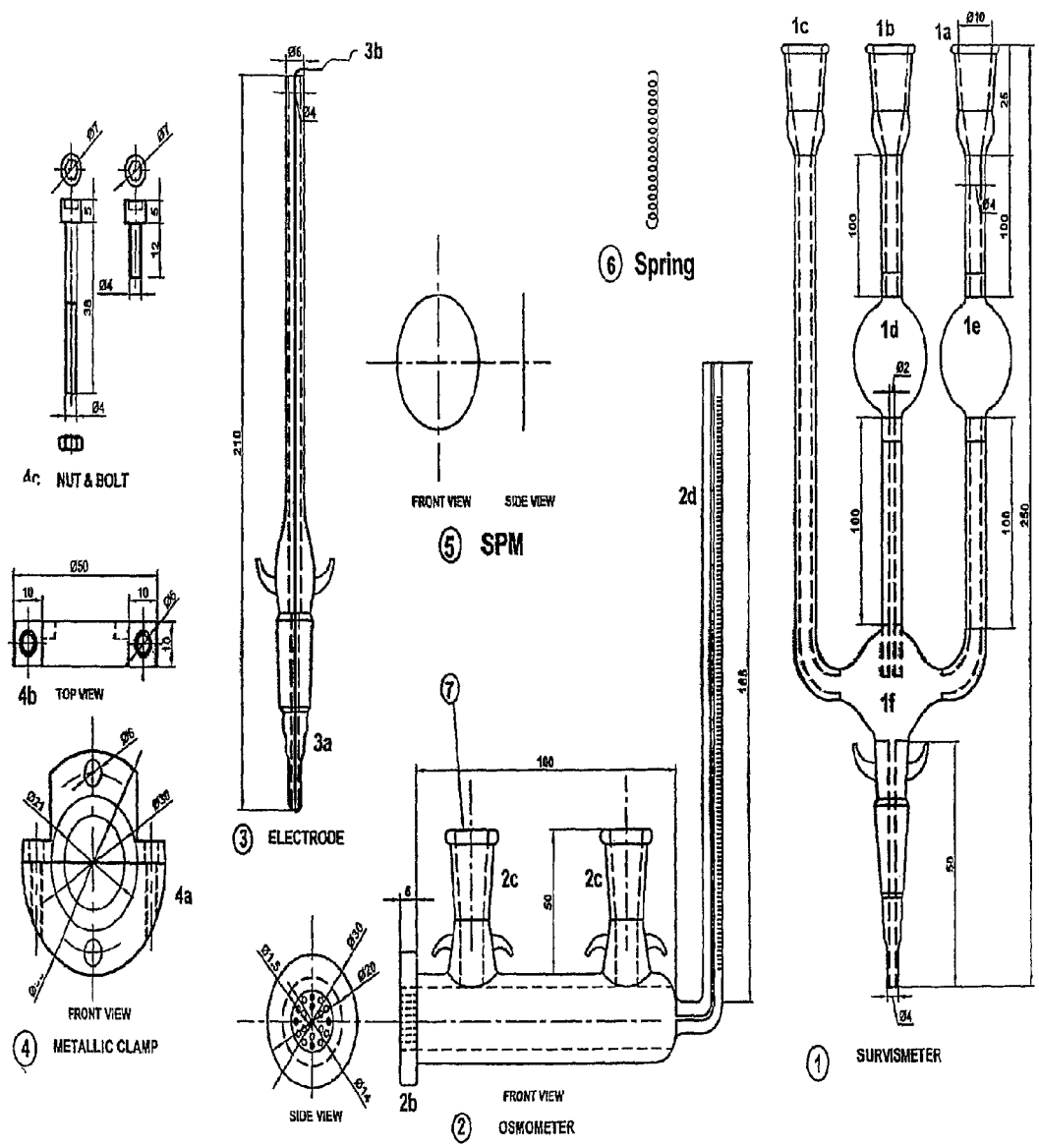
Figure 2: COMPONENTS OF OSCOSURVISMETER

APPARATUS FOR MEASURING OSMOTIC PRESSURE, CONDUCTANCE, VISCOSITY AND SURFACE TENSION OF LIQUID SOLUTION

FIELD OF INVENTION

The present invention relates to an apparatus for measuring osmotic pressure, surface tension, viscosity and conductance of a test solution/liquid.

BACKGROUND OF THE INVENTION

Until now the determination of liquid properties such as osmotic pressure, conductance, surface tension, viscosity are carried out with the help of separate instruments. If all the four properties of the same test solution are to be measured, then it's a time consuming process and the liquid or test solution gets wasted. Also, the nature of biological fluids or solutions of great biophysical, physiological and physiochemical significance do not allow their exposure for longer period for measuring such properties. Due to this reason the time and material saving technology is gaining ground thus the present invention is an important step forward in reducing multi-step operations in handling of solutions for measuring any of the physical properties. Otherwise it involves transfer of the solution to different cells for different detectors for each of the property where solutions are prepared afresh, where much of the amount of the chemicals and distilled water or solvents is utilized involving many glass wares. These properties are of industrial use as the viscosity of solvent plays crucial role for mobility/$m^2s^{-1}v^{-1}$ of cations and anions in osmotic process and syrup mobility/$m^2s^{-1}v^{-1}$ in buffers under applied field strength IV $m^{-1}$. The conductance, viscosity and surface tension values for process of hydrophobic sols are slightly lower than that of water having least variation with concentration while hydrophilic sols predict reverse relation. These data authentically predict the critical micelle concentration (CMC) point while membrane osmometry is most important for the group as far as synthetic polymers are concerned.

OBJECT OF THE PRESENT INVENTION

The main object of the present invention is provide an apparatus for measuring osmotic pressure, surface tension, viscosity and conductance of a test solution/liquid.

SUMMARY OF THE INVENTION

The present invention provides an apparatus (Oscosurvismeter) for measuring osmotic pressure, surface tension, viscosity and conductance of a test solution/liquid. Particularly, in the apparatus (Oscosurvismeter) of the present invention four different detectors are attached to single unit for measuring the said properties with a single apparatus.

BRIEF DESCRIPTION OF THE DRAWINGS

FIG. 1 is an exemplary illustration of the apparatus (Oscosurvismeter) for measuring osmotic pressure, surface tension, viscosity and conductance of a test solution/liquid.

FIG. 2 is an exemplary illustration of the different components of the apparatus (Oscosurvismeter) of the present invention.

STATEMENT OF THE INVENTION

Accordingly, the present invention relates to an apparatus for measuring osmotic pressure, surface tension, viscosity and conductance of a test solution/liquid, said apparatus comprising: at least two cells (2) fitted together thereby forming a vessel (2a) suitable for holding the test solution/liquid; said vessel (2a) comprises: (a) a semi permeable membrane (5) disposed between the two opposite ends of the cells (2); (b) at least two capillaries (2d) vertically fitted to the two opposite ends of the vessel (2a); (c) one or more slots (8) are being provided in order to accommodate survismeter (1) and electrodes (3) for measuring the said desired properties.

DETAIL DESCRIPTION OF THE PRESENT INVENTION

Accordingly, the present invention relates to an apparatus for measuring osmotic pressure, surface tension, viscosity and conductance of a test solution/liquid, said apparatus comprising:

at least two cells (2) fitted together thereby forming a vessel (2a) suitable for holding the test solution/liquid; said vessel (2a) comprises:
- (a) a semi permeable membrane (5) disposed between the two opposite ends of the cells (2);
- (b) at least two capillaries (2d) vertically fitted to the two opposite ends of the vessel (2a);
- (c) one or more slots (8) are being provided in order to accommodate survismeter (1) and electrodes (3) for measuring the said desired properties.

In an embodiment of the present invention the cells are connected to each other by connecting means selected from a group comprising glue, metallic rings/clamps, metallic screws, rivets, to avoid leakage of the test solution/liquid.

In another embodiment of the present invention the survismeter (1) comprising:
- (a) three capillaries; at least two of the said capillaries having one or more bulb/chambers (1d, 1e) and;
- (b) a bulb/chamber (1f) at the common connecting location of the three capillaries;
- (c) an inlet (9) adapted to be connected with one of the slots (8) provided on the vessel (2a);

wherein the upper ends of the capillaries are in the form of sockets (1a, 1b, 1c).

In still another embodiment of the present invention the electrodes (3) are in contact with the test solution/liquid for measuring the conductance of test solution/liquid.

In a further embodiment of the present invention the slots (8) are provided with sockets (2c) connecting survismeter and electrodes.

In one more embodiment of the apparatus the survismeter (1) and the electrodes (3) are connected to the sockets (2c) with the help of a connecting means selected from a group comprising springs, resilient materials etc.

In another embodiment of the present invention one of the slots (8) is provided with socket (7) as inlet for supplying test solution/liquid in the vessel.

In sill another embodiment of the present invention the slots (8) provided on the vessel are equidistant.

In one more embodiment of the present invention the capillaries (2d) are graduated with suitable markings for calculating osmotic pressure.

The present invention is described with reference to the figures and specific embodiments; this description is not meant to be construed in a limiting sense. Various alternate embodiments of the invention, will become apparent to persons skilled in the art upon reference to the description of the invention. It is therefore contemplated that such alternative embodiments form part of the present invention.

FIGS. 1 and 2 illustrates the apparatus and different component of the apparatus according to one of the embodiment of the present invention. The apparatus of the present invention comprises at least two cells (2) preferably cylindrical. The cells (2) are attached to each other but attachment means and forms a vessel (2a) for containing test solution/liquid. The attachment means are but not limited to clamps, nut-blots, screws, rivets, glue etc. A semi-permeable membrane (5) is provided at a suitable location in the vessel thereby dividing the vessel in two parts. The Semi-peameable membrane can be disposed between the two opposite ends of the osmometer cells before attaching the two cells. The pore size of the Semi-peameable membrane can be selected depending upon the selection of test solution/liquid. There are two capillaries (2d) provided at the two ends of the vessel. The capillaries are preferably vertical and graduated in order to take measurements.

The vessel is provided with one or more slots (8). The number of slots is preferably four and equally spaced longitudinally. Slots are provided with sockets (2c) in order to accommodate survismeter (1) and electrodes (3). Survismeter is a unit for measuring surface tension and viscosity. The electrodes are connected to a conductivity bridge for measuring conductance. The location of the survismeter and electrodes can be changed which may vary the values of properties. The Survismeter preferably comprises three capillaries. Out of three capillaries two capillaries have bulb/chamber (1d, 1e). The capillaries having bulb/chamber is provided with upper and lower marks to facilitate the precise measurement of the properties. The three capillaries of the Survismeter are connected to each other by a major bulb/chamber (1f). An inlet (9) is provided with the major bulb (1f). The inlet of the major bulb/chamber or in other words the inlet of the survismeter is connected to one of the sockets provided on the vessel. The inlet of the survismeter and the electrodes are inserted in the sockets in such a manner that the inlet of the survismeter and electrodes come in contact with the test solution/liquid. The inlet of the survismeter and electrodes are connected to the sockets (2c) with the help of connecting means. Connecting means can be selected for a group comprising springs, resilient materials. The slots can also be provided with threads and the corresponding threads can be provided on the outer cover of the electrodes and the inlet of the survismeter in order to connect slots and survismeter or electrodes. One of the slots provided on the vessel can be used as an inlet for supplying test solution/liquid. The connections such as connections between the survismeter and socket provide on vessel and/or connections between the electrodes and socket are airtight and watertight connections.

As can be noticed from FIG. 1 the apparatus (Oscosurvismeter) of the present invention is a single unit to exactly measure the four parameters and thereby reduces time of measurement and also reduces wastage of test solution/liquid. The apparatus of the present invention is shown in FIG. 1. The assembled unit depicted in FIG. 1 and the individual components are depicted in FIG. 2, it is a four in one device, attached to cells of Osmometer on makeshift arrangement, thus firstly both of the Osmometer cells are fitted together with metallic rings/clamps denoted with number 4 and tightened with metallic screws (FIG. 2, 4a). The front and top views of the metallic clamp are depicted in FIG. 2, 4a and 4b, and nut bolt in 4c. The semi permeable membrane (SPM) denoted with number 5 is sandwiched between the opposite ends of cylindrical cells. The clamp is tightly fitted with metallic screws/nut bolts denoted with number 4c and 4b of FIG. 2 to avoid the entry of the thermostating liquid and leakage of the solution taken in the cells. The extreme left and right ends of the cells fused with the capillaries (2d of FIG. 2) with 0.5 mm internal diameters (1d) for uprising of the liquids with capillary action. The cells are fitted in a manner that their both the capillaries face upward (as shown in FIG. 2) horizontally. The position of each part is made fixed with high potential springs connecting to their hooks as depicted in the FIG. 1, represented by number 6 of FIG. 2. In each joint the silicon vacuum grease was applied for making them air and water tight. Thereafter the Survismeter and electrodes depicted by numbers 1 and 3 respectively are fitted to their corresponding sockets 2c provided on the Osmometer cells (FIG. 2). The B$9 standard ground glass joint at the lower end of Survismeter below its bulb (1f) and similar joints of electrodes in the form of the cones are fitted into the sockets (2c and 2c of FIG. 2) of the cells. The dilute solution/solvent is taken in LHS (left hand side) cell while solution in RHS for experimental measurement through their corresponding sockets. After ensuring the leakage the whole assembly is mounted on the stainless steel stand fitted in the thermostat for temperature control within ±0.01° C., measured with Beckman thermometer. Addition and deletion of the solutions are made through socket (7) (FIG. 1) and also used for fitting the removing the air bubbles if any. Different properties of the liquid/test solution as described hereafter.

Viscosity ($\eta$):

The 1b socket of Survismeter is blocked with stopper and the socket (1c) remains open for pressure control. The upper ends in the form of sockets marked with 1a, 1b and 1c, and the bulbs 1d and 1e are connected to the major bulb (1f) through 0.5 mm capillary for solution sucking and down flow. Now the solution is sucked through $20 \times 10^{-3}$ dm$^3$ capacity syringe to bulb (1e), when solution goes above its upper mark, the sucking is stopped and back flow of the solution is allowed. The L shaped ground glass cone is fitted into the ground glass socket (1a) of stem connecting the bulb (1e) while another end of the cone is fitted with one end of a soft PVC tube, whose another end is fitted with the needle of the syringe. Pushing the plunger of the syringe back, the liquid moves towards the bulbs 1f and then to 1e, respectively, when the liquid goes above the mark of the bulb 1e, the sucking is stopped and back flow is permitted. The efflux time of the solution with electronic racer of $1 \times 10^{-2}$ s$^{-1}$ within the two marks made on the capillary upper and lower of the 1f bulb is noted down after opening the socket 1b. The latter helps in solution filling and downward flow for efflux times and drop wise flow, and from the data of flow times, the viscosity values are calculated given elsewhere[1].

Surface tension ($\gamma$):

Similarly the 1a socket is blocked with stopper and solutions is sucked in 1f and then to bulb 1d for drop wise flow for the determination of the surface tension. When the solution goes above the upper mark the forward sucking is stopped and backward flow is allowed in the form of the drop formed around the circumference of the tip of the capillary extended in bulb 1d. The drops formed on-flow of the solution between upper and the lower marks are counted manually, the inner diameter (1d) of capillaries of stems between the 1b to 1d and to 1f is 0.5 mm. Drop numbers are put in a usual equation for surface tension calculation[1]. For calibration the measurements are repeated several times for reproducibility.

Osmotic pressure ($\pi$):

Both of the cells of the osmometer adjoined with (4 of FIGS. 1, and 4b and 4c of FIG. 2) metallic clamps of specified dimension are screwed and tightened with the specified L shaped hexagonal metallic tools to sandwich the SPM (FIG. 2, number 5) between the clamps, the nuts of the screws/bolt used are of hexagonal type (FIG. 2 4c). The clamp part was divided into two halves upper and lower (FIG. 2 4a) to tightly hold the semi permeable membrane (SPM) and prevent leakage of the solutions. The assembly (FIG. 1) was put to work, the solvent passes from LHS to the RHS cells generating pressure ($\pi$) in the solution cell and raises the level in the capillary 2d. The semi permeable membrane (SPM) allows solvent molecules to pass through blocking solute, and the hydrostatic pressure (1c) on RHS capillary columns was recorded by means of the heights of the corresponding fluids. Thus sufficient excess osmotic pressure ($\pi$) is generated in RHS and used to calculate activity and activity coefficient of the electrolytes and non-electrolytes. The values of the osmotic pressure ($\pi$) are calculated with equation 1.

$$lm_{c \to 0}\left(\frac{\pi}{c}\right) = \frac{RT}{M} \quad (1)$$

Here, the $\pi$ osmotic pressure, c concentration, M is molecular weight, R is J mol$^{-1}$K$^{-1}$, and the temperature T is in Kelvin. It is most useful to determine molecular weight of the $$\left(\frac{\pi}{c}\right)_{\to 0} = \frac{RT}{M_n^-} \quad (2)$$

polymer substances. Similarly the number average number molecular weight ($\overline{M}_n$) of the polymer substance is calculated from the van't Hoff's equation 2.

Conductance ($\kappa$):

As shown in FIG. 2 Electrodes (3) were fitted and their leads connected to conductivity bridge, the silicon grease was applied on the ground glass cone fitted in the B$9 joint ground socket (FIG. 2 (2c)). The lower tips of the electrodes were kept 4 cm immersed in the solution and connected to the Leads and Northup Conductivity Bridge for measuring the conductivity. Naturally when the molecules are left free to respond to several detectors as specific conductance ($\kappa$), solubility (S) gram equivalent dm$^{-3}$ (g equiv dm$^{-3}$). Thus firstly the cell constant (l/a) m$^{-1}$ is measured with standard aqueous KCl solutions as under.

$$\kappa = \text{Cell constant}(l/a) \times \text{observed conductance}(\Lambda_{obs})$$

The solutions prepared in conductivity water (1×100$^{-7}$ $\Omega$cm$^{-1}$) in Pyrex glass flask were taken in both the cells and thermostated at 25° C. for 30 min. The 1c can measure the $\Lambda_{equiv}$ (equivalent) and $\Lambda_{mol}$ (molar) conductances, and degree of hydrolysis ($\alpha$) as under.

$$\alpha = \Lambda_0 / \Lambda_{inf}$$

The $\Lambda_0$ and $\Lambda_{inf}$ are conductances at zero and infinite dilutions, respectively. The solubility (g equi dm$^{-3}$) is calculated as under.

$$\Lambda_v = \Lambda_{inf} = \Lambda_a^0 + \Lambda_c^0$$

$$\Lambda_v = (1000\kappa)/S$$

$$\kappa = \kappa_{solution} - \Lambda_{water}$$

The study polarity of the systems when the molecules are left free to respond to several detectors as the $\Lambda$, $\pi$, $\eta$ and $\gamma$ properties of the solutions with single instrumental unit.

The $\eta$ and $\gamma$ values measured for solvents are given in table I and of $\pi$ and $\kappa$ values for aqueous solutions of sucrose and KCl, respectively, in tables 2 and 3. The water has been used as solvent for four parameters and the aqueous solutions of known systems have been chosen for the calibration of the Oscosurvismeter. The calibration of the each subunit (Osmometer, Survismeter, Conductivity unit) was made separately. Since the focus has been to check the accurate working of the new instrument, and hence unknown systems are not taken for measurements. The values of the $\eta$ and $\gamma$, and $\pi$ and $\kappa$ data have been measured separately using the corresponding unit and a close agreement in the measured data has been noted with those of the literature data given tables.

TABLE 1

The $\eta$ and $\gamma$ data of the solvents at 298.15 K.

| | 293.15 Exp. $\rho/10^3$ kg m$^{-3}$ | Lit. $\rho/10^3$ kg m$^{-3}$ | $\eta$(Lit*) kg m$^{-1}$s$^{-1}$ | $\eta$(Exp) kg m$^{-1}$s$^{-1}$ | $\gamma$(Lit*.) 10$^{-1}$Nm$^{-1}$ | $\gamma$(Exp) 10$^{-1}$Nm$^{-1}$ |
|---|---|---|---|---|---|---|
| Aniline | 1.01736 | 1.01740 | 1.5940 | 1.5940 | 47.9 | 47.9 |
| CCl$_4$ | 1.58432 | 1.58429 | 1.45704 | 1.45704 | 26.15 | 26.15 |
| Chlorobenzene | 1.10121 | 1.10118 | 1.5219 | 1.5219 | 32.65 | 32.65 |
| O-xylene | 0.87604 | 0.87600 | 1.50295 | 1.50295 | 29.62 | 29.62 |

*Reference no. 2. Levitt B. P. and Kkitchner J. A., Findlay's Practical Physical Chemistry, 1954, 9$^{th}$ Ed. 420-421 PP, Longman London and New York.

TABLE 2

The $\pi$ values of aqueous sucrose measured with Oscosurvismeter and literature values at 293.15 K.

| Conc., mol kg$^{-1}$ | $\pi$ (Lit*), atm | $\pi$ (Exp.), atm | $\Delta\pi$ = Lit. – Exp, atm |
|---|---|---|---|
| 0.1 | 2.59 | 2.60 | −0.01 |
| 0.2 | 5.06 | 5.04 | 0.01 |
| 0.4 | 10.14 | 10.11 | −0.03 |
| 0.7 | 18.13 | 18.15 | −0.02 |
| 1.0 | 26.60 | 26.61 | −0.01 |

*Reference no. 3 and 4 Cole R. H. and Cole J. S., Physical Principles of Chemistry, W. H. Freeman and Company San Francisco and London, 1964, pp. 477-481. Moelwyn-Hughes, E. A., Physical Chemistry, 2$^{nd}$ ed. 1961, pp 803, Pergamon, Oxford.

TABLE 3

The specific conductance ($\kappa$, $\Omega^{-1}$cm$^{-1}$) of KCl solutions (mol kg$^{-1}$) was measured at 298.15 K, temperatures.

| KCl conc. in | $\kappa$ (Lit*.) | $\kappa$ (Exp.) | $\Delta\pi$ = Lit. – Exp. |
|---|---|---|---|
| 1.000 | 0.111730 | 0.111670 | −0.00006 |
| 0.100 | 0.012886 | 0.012876 | −0.000010 |
| 0.020 | 0.00270 | 0.002759 | 0.000059 |

TABLE 3-continued

The specific conductance ($\kappa$, $\Omega^{-1}$cm$^{-1}$) of KCl solutions (mol kg$^{-1}$) was measured at 298.15 K, temperatures.

| KCl conc. in | $\kappa$ (Lit*.) | $\kappa$ (Exp.) | $\Delta\pi$ = Lit. − Exp. |
|---|---|---|---|
| 0.010 | 0.001415 | 0.001419 | 0.000004 |
| 0.001 | 0.0001469 | 0.0001547 | 0.0000078 |

*Reference no. 5 B. D. Khosla, Senior Physical Chemistry, 11$^{th}$ ed., 2002, pp 363, R. Chand and CO., 1, Ansari Road, Daryaganj, New Delhi-110002, India.

I claim:

1. An apparatus for measuring osmotic pressure, surface tension, viscosity and conductance of a test liquid, said apparatus comprising:
    at least two cells fitted together thereby forming a vessel suitable for holding the test liquid; said vessel comprises:
    (a) a semi permeable membrane disposed between the two opposite ends of the cells;
    (b) at least two capillaries vertically fitted to the two opposite ends of the vessel;
    (c) one or more slots are being provided in order to accommodate an inlet and electrodes, said inlet being connected to a common chamber at the connecting location of three capillaries, wherein at least two of said capillaries have one or more chambers.

2. The apparatus according to claim 1, wherein the cells are connected to each other by connecting means selected from a group comprising glue, metallic rings, clamps, metallic screws, and rivets, to avoid leakage of the test liquid.

3. The apparatus according to claim 1, wherein the electrodes are in contact with the test liquid for measuring the conductance of the test liquid.

4. The apparatus according to claim 1, wherein the slots are provided with sockets for connecting to said inlet and connecting to said electrodes.

5. The apparatus according to claim 1, wherein the inlet and the electrodes are connected to the sockets with the help of a connecting means selected from a group comprising springs and resilient materials.

6. The apparatus according to claim 1, wherein one of the slots is provided with a socket for supplying test liquid into the vessel.

7. The apparatus according to claim 1, wherein the slots provided on the vessel are equidistant.

8. The apparatus according to claim 1, wherein the capillaries are graduated with suitable markings for calculating osmotic pressure.

* * * * *